United States Patent
Schader et al.

(10) Patent No.: US 11,071,832 B2
(45) Date of Patent: Jul. 27, 2021

(54) MEDICAMENT INJECTION DEVICE

(71) Applicant: Sanofi-Aventis Deutschland GmbH, Frankfurt am Main (DE)

(72) Inventors: Marc Schader, Frankfurt am Main (DE); Michael Helmer, Frankfurt am Main (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 134 days.

(21) Appl. No.: 15/779,017

(22) PCT Filed: Nov. 21, 2016

(86) PCT No.: PCT/EP2016/078278
§ 371 (c)(1),
(2) Date: May 24, 2018

(87) PCT Pub. No.: WO2017/089288
PCT Pub. Date: Jun. 1, 2017

(65) Prior Publication Data
US 2018/0353708 A1 Dec. 13, 2018

(30) Foreign Application Priority Data
Nov. 27, 2015 (EP) .................................. 15196715

(51) Int. Cl.
*A61M 5/32* (2006.01)
*A61M 5/24* (2006.01)
(Continued)

(52) U.S. Cl.
CPC ............ *A61M 5/3243* (2013.01); *A61M 5/20* (2013.01); *A61M 5/2466* (2013.01); *A61M 5/24* (2013.01);
(Continued)

(58) Field of Classification Search
CPC .............. A61M 5/3243; A61M 5/2466; A61M 2005/2013; A61M 2005/247;
(Continued)

(56) References Cited

U.S. PATENT DOCUMENTS

2007/0073224 A1  3/2007 Dries
2007/0073324 A1  3/2007 Baikoff
(Continued)

FOREIGN PATENT DOCUMENTS

CN    101610804    12/2009
CN    104768596    7/2015
(Continued)

OTHER PUBLICATIONS

International Preliminary Report on Patentability in Application No. PCT/EP2016/078278, dated May 29, 2018, 8 pages.
(Continued)

*Primary Examiner* — Manuel A Mendez
*Assistant Examiner* — Justin L Zamory
(74) *Attorney, Agent, or Firm* — Fish & Richardson P.C.

(57) ABSTRACT

An injection device comprising: a housing arranged to contain a medicament cartridge; a needle holder holding an injection needle; a generally tubular needle sleeve fixed with respect to the needle holder and axially movable with respect to the housing; and a gear assembly comprising a rotary gear fixed to the needle holder, a first gear rack disposed on the needle sleeve and a second gear rack disposed on the housing, wherein the gear assembly is arranged so that movement of the needle sleeve in a proximal axial direction causes movement of the needle holder in the proximal axial direction.

20 Claims, 2 Drawing Sheets

(51) Int. Cl.
*A61M 5/20* (2006.01)
*A61M 5/315* (2006.01)

(52) U.S. Cl.
CPC ............... *A61M 2005/2013* (2013.01); *A61M 2005/247* (2013.01); *A61M 2005/2474* (2013.01); *A61M 2005/3152* (2013.01); *A61M 2005/3267* (2013.01)

(58) Field of Classification Search
CPC .. A61M 2005/2474; A61M 2005/3152; A61M 2005/3267
See application file for complete search history.

(56) References Cited

U.S. PATENT DOCUMENTS

| | | | |
|---|---|---|---|
| 2007/0191784 A1* | 8/2007 | Jacobs | A61M 5/31555 604/224 |
| 2013/0211330 A1* | 8/2013 | Pedersen | A61M 5/2033 604/111 |
| 2017/0080165 A1* | 3/2017 | Soerensen | A61M 5/2466 |

FOREIGN PATENT DOCUMENTS

| | | |
|---|---|---|
| EP | 2468329 | 6/2012 |
| JP | 2005-524447 | 8/2005 |
| JP | 2010-509958 | 4/2010 |
| JP | 2012-525869 | 10/2012 |
| JP | 2015-532191 | 11/2015 |
| WO | WO 2003/092771 | 11/2003 |
| WO | WO 2008/058666 | 5/2008 |
| WO | WO 2012/022810 | 2/2012 |
| WO | WO 2012/085032 | 6/2012 |
| WO | WO 2014/064100 | 5/2014 |
| WO | WO 2014/068098 | 5/2014 |
| WO | WO 2015/055592 | 4/2015 |
| WO | WO 2015/140262 | 9/2015 |

OTHER PUBLICATIONS

International Search Report and Written Opinion in Application No. PCT/EP2016/078278, dated Feb. 20, 2017, 13 pages.

* cited by examiner

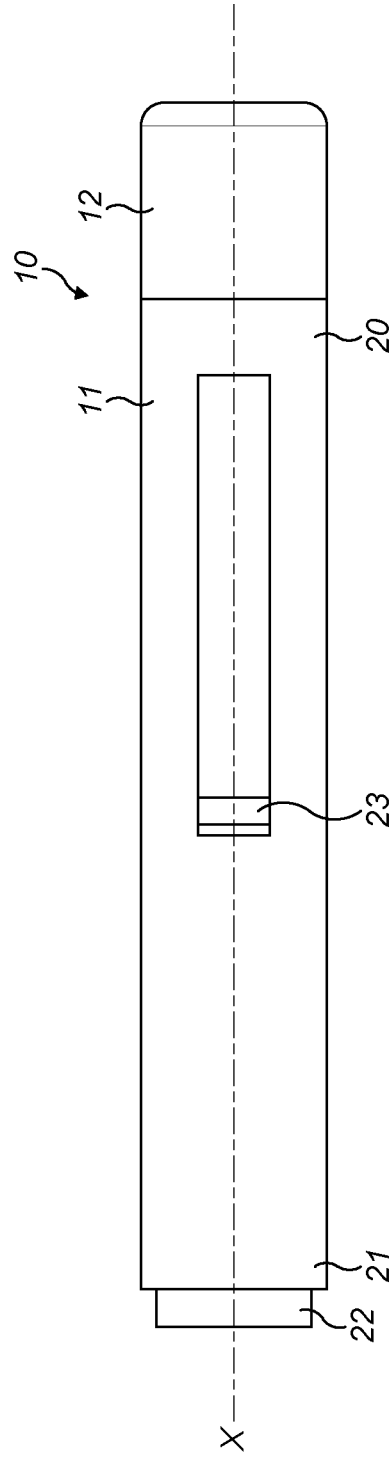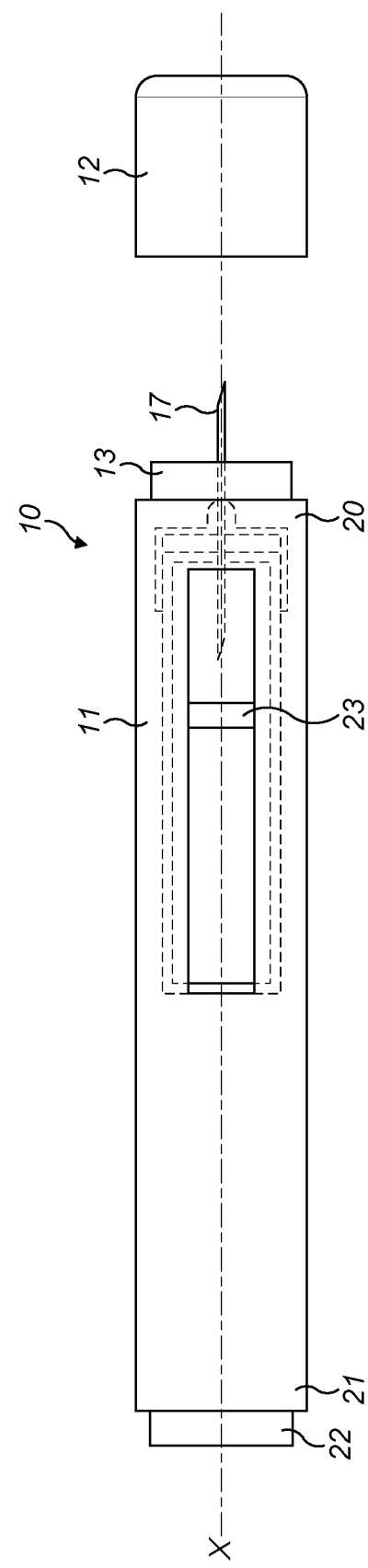

MEDICAMENT INJECTION DEVICE

CROSS REFERENCE TO RELATED APPLICATIONS

This application is a U.S. national stage application under 35 USC § 371 of International Patent Application No. PCT/EP2016/078278, filed on Nov. 21, 2016, which claims priority to European Patent Application No. 15196715.5, filed on Nov. 27, 2015, the entire contents of each of which are incorporated herein by reference.

TECHNICAL FIELD

The disclosure generally relates to medicament injection devices

BACKGROUND

Medicament injection devices can take the form of a syringe, whereby medicament is provided in a tubular barrel having a plunger and an outlet to which a needle is connected. A user connects the needle to the reservoir manually before the injection takes place. The attachment of the needle to the syringe requires some dexterity and is difficult for those having poor coordination, such as patients who have lost a degree of sensation in their hands.

While it is possible to provide injection devices in which the needle is pre-attached to a medicament cartridge, in certain situations it is desirable to provide a device in which the needle is kept separate from the medicament until such time as the user wishes to commence the injection.

SUMMARY

According to a first embodiment there is provided an injection device comprising: a housing arranged to contain a medicament cartridge; a needle holder holding an injection needle; a generally tubular needle sleeve fixed with respect to the needle holder and axially movable with respect to the housing; and a gear assembly comprising a rotary gear fixed to the needle holder, a first gear rack disposed on the needle sleeve and a second gear rack disposed on the housing, wherein the gear assembly is arranged so that movement of the needle sleeve in a proximal axial direction causes movement of the needle holder in the proximal axial direction.

The first and second gear racks may be circumferentially opposite to each other.

The housing may comprise a cartridge holder having a generally tubular profile.

The second gear rack may be disposed on an inwardly facing surface of the cartridge holder at a distal end thereof.

The device may contain a medicament cartridge.

The cartridge may comprise a pierceable septum at a distal end thereof, and wherein the injection needle is arranged to pierce the pierceable septum when the needle holder is urged in the proximal direction.

The cartridge may contain a medicament.

The device may further comprise a cap that is removably engaged with the housing.

The device may be an auto-injector.

The rotary gear may have a plurality of teeth arranged circumferentially around the gear.

The rotary gear may comprise a circumferential portion with no teeth thereon.

The needle holder may comprise a hollowed recess in the centre thereof to accommodate the distal end portion of a cartridge.

The needle holder may comprise an engaging element configured to lock the distal end portion of the cartridge.

A second embodiment provides a method of operating an injection device, the method comprising: pushing a needle sleeve in a proximal axial direction, thereby causing a linear gear rack disposed thereon to rotate a rotary gear to cause axial displacement of a needle holder in a proximal direction.

BRIEF DESCRIPTION OF THE DRAWINGS

So that the present disclosure can be fully understood, embodiments thereof will be described with reference to the accompanying drawings, in which:

FIGS. 1A and 1B are side-on views of an auto-injector device according to some embodiments;

DETAILED DESCRIPTION

Figure 2:
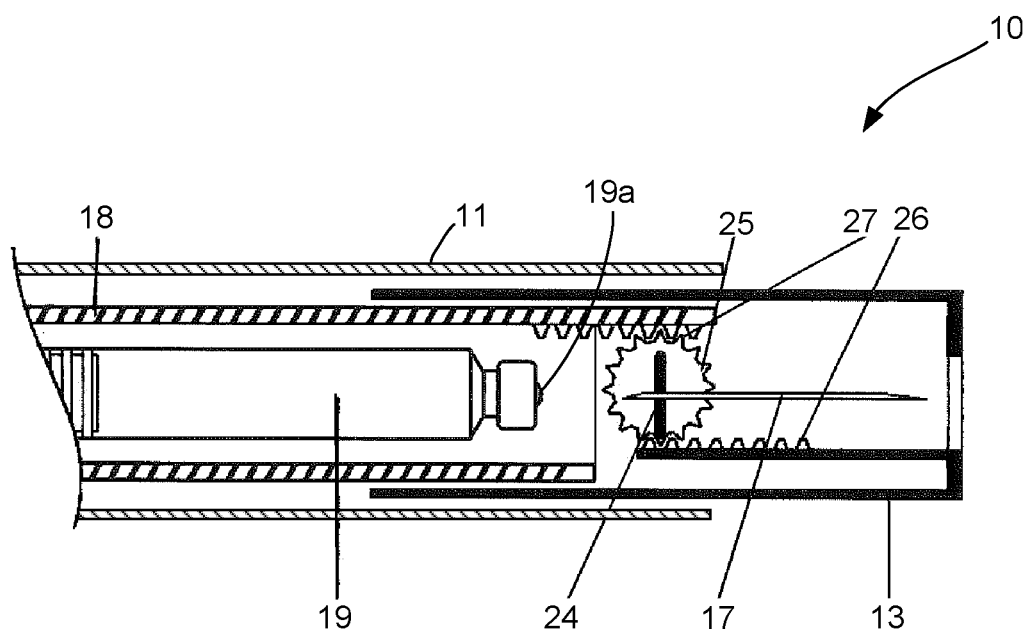
FIG. 2 is a side-on cross sectional view of the distal end of the device shown in FIGS. 1A and 1B prior to insertion of the needle into the cartridge.

Some embodiments provide a mechanism for inserting the needle of an injection device such as an auto-injector or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in some embodiments the user does not need to touch the needle during the steps of inserting the needle into the medicament cartridge and subsequently actuating the injection of the medicament.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17. Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 is a schematic cross-sectional view of part of an injection device in an initial state after the cap 12 has been removed. A cartridge holder 18 holding a cartridge 19 is contained within the housing 11. The cartridge holder 18 is fixed with respect to the housing 11.

The cartridge 19 comprises a pierceable septum 19a at its distal end, and contains liquid medicament which is to be delivered to a patient during injection. The cartridge 19 comprises a distal end portion which is shaped to be accommodated into a recess of a needle holder 24. The needle holder 24 is located near a distal end of the cartridge 19. The needle holder 24 holds the hollow injection needle 17 which, in an initial state, is not in contact with the pierceable septum 19a of the cartridge 19, as can be seen in FIG. 2.

The needle 17 comprises sharp ends at both the proximal and distal ends thereof so that the needle can pierce both the septum 19a of the cartridge 19 and the patient's skin.

In some embodiments, a proximal end of the needle 17 pierces the septum 19a of the cartridge automatically as the sleeve 13 is pushed in a proximal direction. Proximal movement of the sleeve 13 to cause the needle 17 to pierce the cartridge septum 19a can be done as part of the same step as the injection. In other words, the distal end 20 of the device 10 may be placed against the injection site and a single continuous action by the user causes both the needle holder to move proximally towards and to pierce the cartridge septum 19a as well as causing the distal end of the needle 17 to emerge from the sleeve 13 and penetrate the patient's skin.

Alternatively, a two step process may be provided. Firstly, the user pushes the sleeve 13 in a proximal direction until the needle 17 pierces the septum 19a. This may be accompanied by audible feedback. As a subsequent step, the user may then commence the injection by pushing the distal end of the device 10 against the injection site.

The device 10 comprises a rotary gear 25. The rotary gear 25 is a toothed wheel that is arranged between first and second linear gear racks 26, 27. The first linear gear rack 26 is provided on a radially-inward facing surface of the needle sleeve 13 towards the distal end of the needle sleeve 13. The second linear rack 27 is arranged on a radially-inward facing surface of the cartridge holder 18 at a distal end thereof. The first and second linear gear racks 26, 27 may be arranged so that are circumferentially opposite one another.

The rotary gear 25 is pivoted on a shaft on the needle holder 24 or on an additional part which acts as a slide and is fixated to the needle holder 24. The needle holder 24 may comprise a hollowed recess in the centre so as to accommodate the distal end portion of the cartridge 19. The needle holder 24 may also comprise an engaging element which is configured to lock the distal end portion of the cartridge 19 in place once it has fitted into the hollowed recess of the needle holder 24. The needle holder 24 is mounted to the sleeve 13 so it can be driven axially by the rotary gear 25.

Figure 3:
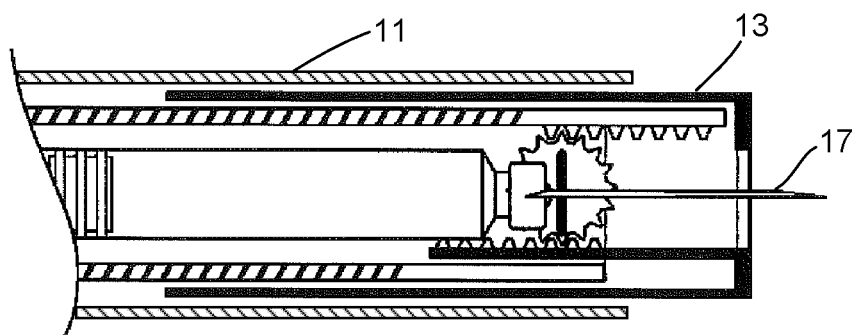
FIG. 3 is a side-on cross sectional view of the distal end of the device shown in FIGS. 1A and 1B after insertion of the needle into the cartridge.

By pushing the sleeve 13 in a proximal direction, the gear racks 26, 27 drive the rotary gear 25 so that the needle 17 moves towards the cartridge 19 and pierces the septum 19a thereof. This is shown in FIG. 3.

For further movement of the sleeve, in some embodiments the rotary gear 25 or gear rack may disengage. The disengagement may be brought about by providing a rotary gear 25 having a circumferential portion with no teeth thereon so that the rotary gear 25 disengages from the first linear rack 26 disposed on the sleeve 13. Alternatively, a latch may be provided to disengage the rotary gear 25 from the first linear rack 26. The injection can then be activated in a manner described above. After the injection, the sleeve 13 returns to the initial position shown in FIG. 2.

In some embodiments, the needle 17 moves forwards with the sleeve 13 in a distal direction to the position shown in FIG. 2.

Alternatively, the engagement between the first gear rack 26 and the rotary gear 25 is released so the gear rack 26, 27 do not drive the needle holder 24 any more.

The injection device 10 comprises a removable cap 12. A needle shield may be provided within the removable cap 12. The distal end of the hollow injection needle 17 may be covered by the needle shield arranged within the removable cap 12 when the removable cap 12 is engaged with the housing 11.

The rotary gear 25 is a pinion gear rotatably mounted between the cartridge holder and the needle sleeve 13 such that the teeth of the rotary gear 25 are engaged with both the teeth of the first linear gear rack 26 and the second linear gear rack 27. The gear assembly is configured such that linear movement of the needle sleeve 13 in a proximal direction (i.e. into the housing 11) rotates the rotary gear 25, thereby causing a linear movement of the needle holder 24 also in a proximal direction.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(o-carboxyheptadecanoyl)-des(B30) human insulin and B29-N-(o-carboxyheptadecanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

What is claimed is:

1. An injection device comprising:
a cartridge holder arranged to contain a medicament cartridge;
a needle holder holding an injection needle;
a generally tubular needle sleeve axially movable with respect to the needle holder and axially movable with respect to the cartridge holder; and
a gear assembly comprising a rotary gear fixed to the needle holder, a first gear rack disposed on the needle sleeve and a second gear rack disposed on the cartridge holder,
wherein the gear assembly is arranged so that movement of the needle sleeve in a proximal axial direction causes movement of the cartridge holder in a distal axial direction.

2. The injection device of claim 1, wherein the first and second gear racks are circumferentially opposite to each other.

3. The injection device of claim 1, wherein the cartridge holder has a generally tubular profile and is comprised in a housing of the injection device.

4. The injection device of claim 1, wherein the second gear rack is disposed on an inwardly facing surface of the cartridge holder at a distal end thereof.

5. The injection device of claim 1, further comprising a medicament cartridge.

6. The injection device of claim 5, wherein the medicament cartridge comprises a pierceable septum at a distal end thereof, and wherein the injection needle is arranged to pierce the pierceable septum when the cartridge holder is urged in the distal axial direction.

7. The injection device of claim 5, wherein the medicament cartridge contains a medicament.

8. The injection device of claim 1, further comprising a cap that is removably engaged with a housing of the injection device.

9. The injection device of claim 1, wherein the injection device is an auto-injector.

10. The injection device of claim 1, wherein the rotary gear comprises a plurality of teeth arranged circumferentially around the rotary gear.

11. The injection device of claim 10, wherein the rotary gear comprises a circumferential portion with no teeth thereon.

12. The injection device of claim 1, wherein the needle holder comprises a hollowed recess in a center thereof to accommodate a distal end portion of a medicament cartridge.

13. The injection device of claim 12, wherein the needle holder comprises an engaging element configured to lock the distal end portion of the medicament cartridge.

14. The injection device of claim 1, wherein the needle sleeve is axially movable relative to the cartridge holder.

15. The injection device of claim 1, wherein the needle holder is fixed relative to a housing of the injection device and the cartridge holder is slidably attached to the housing.

16. A method of operating an injection device, the method comprising:
pushing a needle sleeve in a proximal axial direction, thereby causing a linear gear rack disposed thereon to rotate a rotary gear to cause axial displacement of a cartridge holder in a distal direction, and
ejecting medicament through a needle when the cartridge holder is in a distal position and the needle sleeve is in a proximal position.

17. The method of claim 16, further comprising piercing a septum of a medicament cartridge attached to the cartridge holder with the needle.

18. The method of claim 16, further comprising moving the needle relative to the cartridge holder and the needle sleeve.

19. The method of claim 16, further comprising moving the needle sleeve relative to the cartridge holder.

20. A method of operating an injection device, the method comprising:
pushing a needle sleeve in a proximal axial direction, thereby causing a linear gear rack disposed thereon to rotate a rotary gear to cause axial displacement of a cartridge holder in a distal direction, and moving a needle relative to the cartridge holder and the needle sleeve.

\* \* \* \* \*